United States Patent [19]

Coburn

[11] Patent Number: 6,004,976

[45] Date of Patent: Dec. 21, 1999

[54] THROMBIN INHIBITORS

[75] Inventor: Craig Coburn, Skippack, Pa.

[73] Assignee: Merck & Co., Inc., Rahway, N.J.

[21] Appl. No.: 09/203,117

[22] Filed: Dec. 1, 1998

Related U.S. Application Data

[60] Provisional application No. 60/067,096, Dec. 1, 1997.

[51] Int. Cl.⁶ .................. A61K 31/435; C07D 471/04
[52] U.S. Cl. ............................. 514/303; 546/118
[58] Field of Search ............................. 546/118; 514/303

[56] References Cited

U.S. PATENT DOCUMENTS 5,658,930  8/1997  Tamura et al. ........................ 514/318

OTHER PUBLICATIONS

Bantick, et al., "New Non–Peptide Angiotensin II Receptor Antagonists . . . ," *Bioorg. Med. Chem. Letters*, vol. 4, No. 1, pp. 127–132 (1994).

Brown, et al., "Design of Orally Active, Non–Peptidic Inhibitors of Human Leukocyte Elastase," *J. Med. Chem.*, vol. 37, No. 9, pp. 1259–1261 (1994).

*Primary Examiner*—Bernard Dentz
*Attorney, Agent, or Firm*—Richard S. Parr; Melvin Winokur

[57] ABSTRACT

A compound which inhibits human thrombin and where has the structure

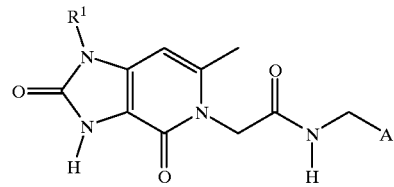

such as

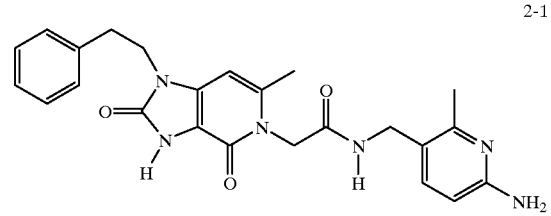

12 Claims, No Drawings

THROMBIN INHIBITORS

This application claims priority of Provisional Application Ser. No. 60/067,096 filed Dec. 1, 1997.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., J. Amer. Chem. Soc. (1992) vol. 114, pp. 1854–63, describes peptidyl α-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or α-keto carboxyl derivatives.

Thrombin inhibitors described in prior publications contain sidechains of arginine and lysine. These structures show low selectivity for thrombin over other trypsin-like enzymes. Some of them show toxicity of hypotension and liver toxicity.

European Publication 601 459 describes sulfonamido heterocyclic thrombin inhibitors, such as N-[4-[(aminoiminomethyl)amino]butyl]-1-[N-(2-naphthalenylsulfonyl)-L-phenylalanyl]-L-prolinamide.

WO 94/29336 describes compounds which are useful as thrombin inhibitors.

Compounds of the invention are bicyclic pyridone thrombin inhibitors. Dornow et al., Chem. Ber., Vol. 99, pp. 244–253 (1966) describes a procedure for making bicyclic pyridones.

SUMMARY OF THE INVENTION

The invention relates to compounds of the formula:

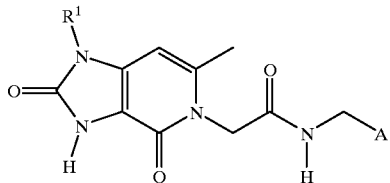

wherein
R1 is selected from the group consisting of
  hydrogen,
  $C_{1-6}$ alkyl,
  $C_{2-6}$ alkenyl,
  $C_{2-6}$ alkynyl,
  $C_{3-8}$ cycloalkyl,
  $C_{3-8}$ cycloalkyl $C_{1-6}$alkyl-,
  aryl,
  aryl $C_{1-6}$ alkyl-, wherein aryl is unsubstituted or substituted with —OH, —NH$_2$, $C_{1-6}$alkyl, $C_{3-8}$cycloalkyl, or halogen, and heteroaryl $C_{1-6}$ alkyl-, wherein heteroaryl is unsubstituted or substituted with —OH, —NH$_2$, $C_{1-6}$alkyl, $C_{3-8}$ cycloalkyl, or halogen;

A is

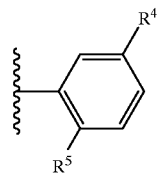

wherein $R^4$ and $R^5$ are independently selected from the group consisting of
hydrogen,
$C_{1-4}$ alkyl,
$C_{2-4}$ alkenyl,
$C_{2-4}$ alkynyl,
$C_{1-4}$ alkoxy,
halogen,
—COOH,
—OH,
—COOR$^7$, where R$^7$ is $C_{1-4}$alkyl,
—CONR$^8$R$^9$, where R$^8$ and R$^9$ are independently
hydrogen or $C_{1-4}$alkyl,
—OCH$_2$CO$_2$H,
—OCH$_2$CO$_2$CH$_3$,
—OCH$_2$CO$_2$(CH$_2$)$_{1-3}$CH$_3$,
—O(CH$_2$)$_{1-3}$C(O)NR$^{10}$R$^{11}$, wherein R$^{10}$ and R$^{11}$ are independently hydrogen, $C_{1-4}$alkyl, $C_{3-7}$ cycloalkyl, or —CH$_2$CF$_3$,
—(CH$_2$)$_{1-4}$OH,
—NHC(O)CH$_3$,
—NHC(O)CF$_3$,
—NHSO$_2$CH$_3$,
—SO$_2$NH$_2$;
or A is

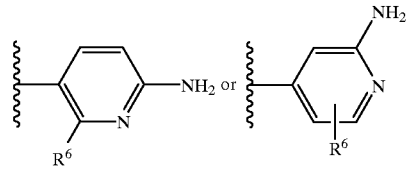

wherein R$^6$ is
hydrogen,
$C_{1-6}$ alkyl,
$C_{2-6}$ alkenyl,
$C_{2-6}$ alkynyl,
$C_{3-8}$ cycloalkyl,
aryl,
aryl $C_{1-6}$alkyl-,
  wherein aryl is an unsaturated 6-carbon ring, either unsubstituted or substituted with —OH, —NH$_2$, $C_{1-6}$alkyl, $C_{3-8}$ cycloalkyl, or halogen.

and pharmaceutically acceptable salts thereof.

In a class of compounds of the invention, A is

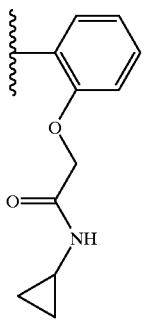

or

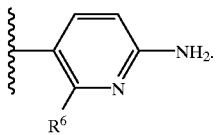

In a subclass of this class, $R^6$ is —$CH_3$.

In a group of this subclass, $R^1$ is selected from the group consisting of $C_{1-6}$ alkyl, $C_{3-8}$cycloalkyl $C_{1-6}$alkyl, aryl $C_{1-6}$alkyl and heteroaryl $C_{1-6}$alkyl.

Exemplary compounds of the invention include

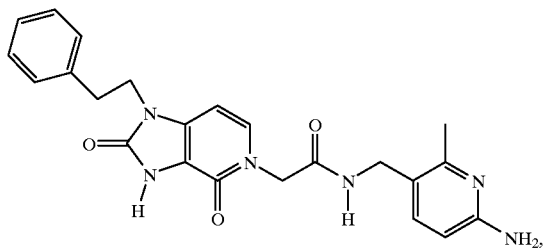

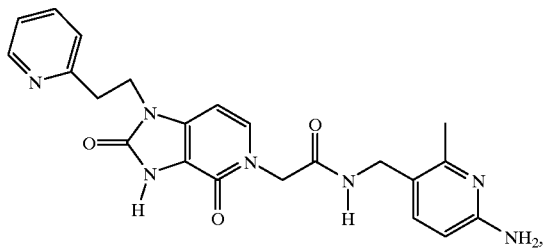

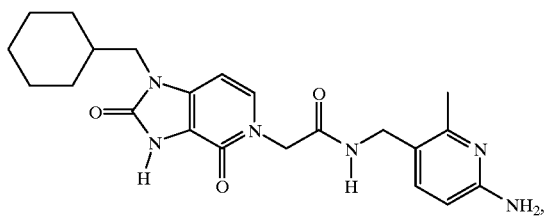

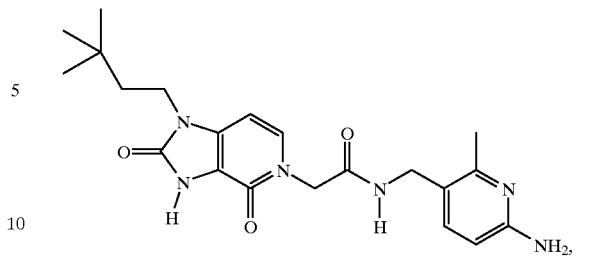

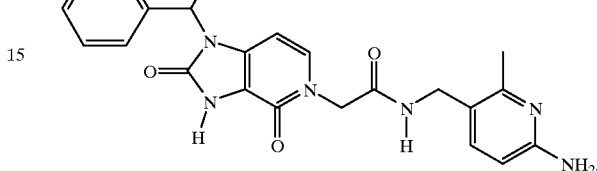

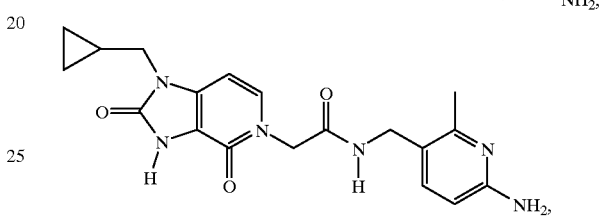

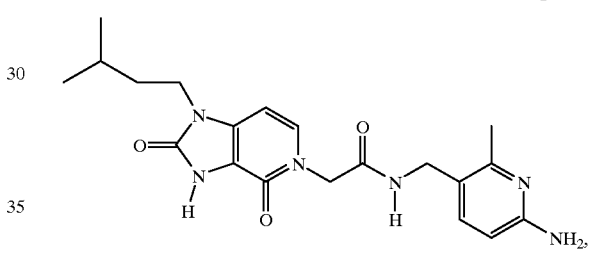

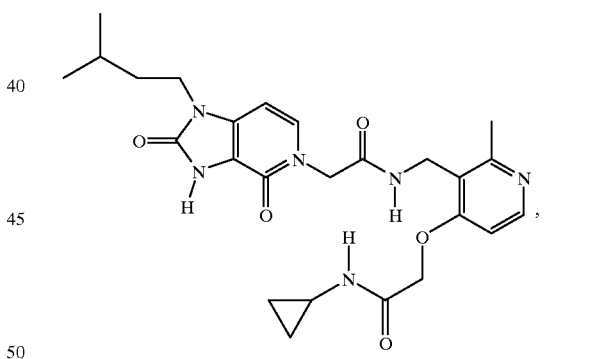

and pharmaceutically acceptable salts thereof.

The pharmaceutically-acceptable salts of the compounds of the invention (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others.

The compounds of the present invention may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention.

When any variable occurs more than one time in any constituent or in formula I, its definition on each occurrence is independent of its definition at every other occurrence. Also, combinations of substituents and/or variables are permissible only if such combinations result in stable compounds.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes a composition for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

The invention also includes the use of a compound of the invention, or a pharmaceutically acceptable salt thereof, in the manufacture of a medicament for inhibiting thrombus formation, preventing thrombus formation, inhibiting thrombin, inhibiting formation of fibrin, and inhibiting formation of blood platelet aggregates, in a mammal.

DETAILED DESCRIPTION OF THE INVENTION

Compounds of the present invention, which are thrombin inhibitors, are useful in anticoagulant therapy. Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Specific embodiments of compounds of the invention are shown in the table below. These compounds inhibit thrombin with the following potency according to in vitro measurements (where "*" means Ki of <10 nM, and "***" means Ki of >10 nM):

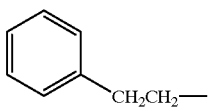

| R$^1$ | A | Ki(nM) |
|---|---|---|
| 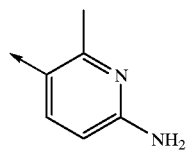 | 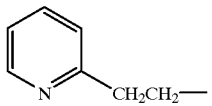 | * |
| 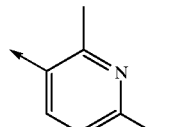 | | * | and pharmaceutically acceptable salts thereof.

In Vitro Assay for Determining Proteinase Inhibition

Assays of human α-thrombin and human trypsin were performed at 25° C. in 0.05 M TRIS buffer pH 7.4, 0.15 M NaCl, 0.1% PEG. Trypsin assays also contained 1 mM $CaCl_2$.

In assays wherein rates of hydrolysis of a p-nitroanilide (pna) substrate were determined, a Thermomax 96-well plate reader was used to measure (at 405 nm) the time dependent appearance of p-nitroaniline. sar-PR-pna (sarcosine-Pro-Arg-p-nitroanilide) was used to assay human α-thrombin (Km=125 μM) and human trypsin (Km=59 μM). p-Nitroanilide substrate concentration was determined from measurements of absorbance at 342 nm using an extinction coefficient of 8270 cm−1M−1.

In certain studies with potent inhibitors (Ki<10 nM) where the degree of inhibition of thrombin was high, a more sensitive activity assay was employed. In this assay the rate of thrombin catalyzed hydrolysis of the fluorogenic substrate Z-GPR-afc (Cbz-Gly-Pro-Arg-7-amino-4-trifluoromethyl coumarin) (Km=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration≦0.5 Km into a solution containing enzyme or enzyme equilibrated with inhibitor. Times required to achieve equilibration between enzyme and inhibitor were determined in control experiments. Initial velocities of product formation in the absence (Vo) or presence of inhibitor (Vi) were measured. Assuming competitive inhibition, and that unity is negligible compared Km/[S], [I]/e, and [I]/e (where [S], [I], and e respectively represent the total concentrations, of substrate, inhibitor and enzyme), the equilibrium constant (Ki) for dissociation of the inhibitor from the enzyme can be obtained from the dependence of Vo/Vi on [I] shown in equation 1.

$$Vo/Vi = 1 + [I]/Ki \tag{1}$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents a linear or branched alkyl group of indicated number of carbon atoms attached through an oxygen bridge; "Halo" or "halogen" as used herein, means fluoro, chloro, bromo and iodo; and "counterion" is used to represent a small, single negatively-charged species, such as chloride, bromide, hydroxide, acetate, trifluoroacetate, perchlorate, nitrate, benzoate, maleate, sulfate, tartrate, hemitartrate, benzene sulfonate, and the like.

The term "$C_{3-7}$cycloalkyl" is intended to include cyclopropyl, cyclobutyl, cyclopentyl, cyclohexyl and cycloheptyl, and the like.

The term "$C_{7-12}$ bicyclic alkyl" is intended to include bicyclo[2.2.1]heptyl (norbornyl), bicyclo[2.2.2]octyl, 1,1,3-trimethylbicyclo[2.2.1]heptyl (bornyl), and the like.

The term "aryl" as used herein except where noted, represents a stable 6- to 10-membered mono- or bicyclic ring system such as phenyl, or naphthyl. The aryl ring can be unsubstituted or substituted with one or more of $C_{1-4}$ lower alkyl; hydroxy; alkoxy; halogen; amino. The term "heteroaryl" refers to a 5- to 7-membered unsaturated ring containing 1 or 2 heteroatoms selected from O, N, or S.

The term "heterocycle" or "heterocyclic ring", as used herein except where noted, represents a stable 5- to 7-membered mono- or bicyclic or stable 9- to 10-membered bicyclic heterocyclic ring system any ring of which may be saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Bicyclic unsaturated ring systems include bicyclic ring systems which may be partially unsaturated or fully unsaturated. Partially unsaturated bicyclic ring systems include, for example, cyclopentenopyridinyl, benzodioxan, methylenedioxyphenyl groups. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0.1–2.5 mg/kg/day, and most preferably 0.1–0.5 mg/kg/day (unless specificed otherwise, amounts of active ingredients are on free base basis). For example, an 80 kg patient would receive between about 0.8 mg/day and 2.4 g/day, preferably 2–600 mg/day, more preferably 8–200 mg/day, and most preferably 8–40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/mi, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug in choosing an The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

Typical tablet cores suitable for administration of thrombin inhibitors are comprised of, but not limited to, the following amounts of standard ingredients:

| Suggested Ranges of Composition for Excipients in Uncoated Tablet Cores | | | |
| --- | --- | --- | --- |
| Excipient | General Range (%) | Preferred Range (%) | Most Preferred Range (%) |
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including antihypercholesterolemics (e.g. HMG CoA reductase inhibitors such as lovastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

Some abbreviations that may appear in this application are as follows.

| Designation | |
| --- | --- |
| HBT(HOBT or HOBt) | 1-hydroxybenzotriazole hydrate |
| Et₃N or TEA | triethylamine |
| EtOAc | ethyl acetate |
| TFA | trifluoroacetic acid |
| POCl₃ | phosphorous oxychloride |
| MeCN | acetonitrile |
| BnEt₃N+Cl– | benzyl triethyl ammonium chloride |
| NaH | sodium hydride |
| DMF | dimethylformamide |
| EtOH | ethyl alcohol |
| Pd(C) | palladium on activated carbon catalyst |
| CF₃COOH | trifluoroacetic acid |
| DCM | dichloromethane |
| DMSO | Dimethylsulfoxide |
| MgSO₄ | magnesium sulfate |
| CDCl₃ | deuterated chloroform |
| CDI | 1,1'-carbonyldiimidazole |
| THF | tetrahydrofuran |
| EDCI | 1-(3-dimethylaminopropyl)-3-ethylcarbodiimide hydrochloride |
| NMM | N-methylmorpholine |
| CD3OD | deuterated methanol |
| CHCl3 | chloroform |
| CH3OH | methanol |
| NH4OH | ammonium hydroxide |

Compounds of the invention can be prepared according to the following general synthetic strategy: 4-hydroxy-6-methyl-3-nitropyridone is chlorinated with, for example, phosphorous oxychloride, acetonitrile and benzyltriethylammonium chloride, to form

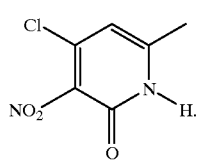

I

I is then alkylated with for example, sodium hydride, dimethyl formamide and tert-butyl bromoacetate, to form

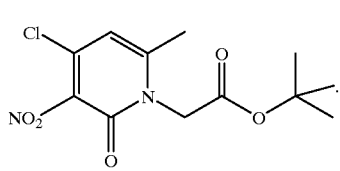

II

R¹NH₂ is then added to II using, for example, ethyl alcohol under heated conditions, to form

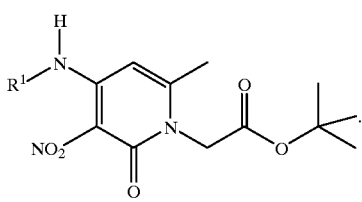

III

Reductive ring closure of III using, for example, hydrogen gas and palladium on activated carbon catalyst, forms

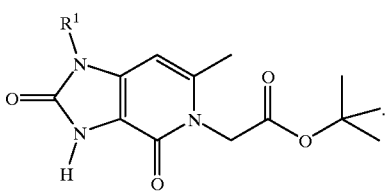

IV

Hydrolysis of IV with, for example, trifluoracetic acid and dicloromethane at around 0° C., forms

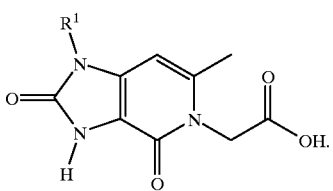

V

Amide coupling of V with ACH2NH2 using, for example, EDCI, 1-hydroxybenzotriazole hydrate, and diisopropylethylamine, forms

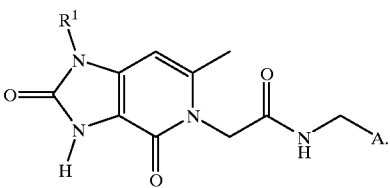

VI

Unless otherwise stated, all NMR determinations were made using 400 MHz field strength.

The following compounds were prepared for use in synthesis of compounds of the invention:

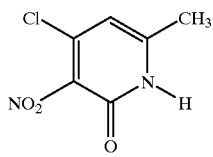

I-1

To a solution of 4-hydroxy-6-methyl-3-nitropyridone (Fluka, 3.15 g, 18.5 mmol) and 16.8 g (74 mmol) of BnEt₃NCl in 65 mL of MeCN was added 7.6 mL (81.4 mmol) of POCl₃. The resulting solution was stirred at 40° C. for 30 min then heated at reflux for 1 h. After evaporation of the solvent, 70 mL of water was added and the mixture was stirred at room temperature for 16 h. The precipitate which formed was filtered and washed with hexane to afford compound I-1 as a yellow solid.

$^1$H NMR (DMSO-$d_6$) d 6.45 (s, 1H), 2.25 (s, 3H).

HPLC $R_f$=0.43.

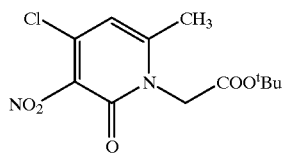

I-2

To a 0° C. solution of 4-chloro-6-methyl-3-nitropyridone (I-1) (3.93 g, 20.8 mmol) in 80 mL of DMF was added 550 mg (22.9 nmnol) of NaH. The resulting solution was stirred at 0° C. for 15 min then treated with 3.69 mL (25.0 mmol) of tert-butylbromo acetate. The homogeneous solution was allowed to stir to room temperature over 16 h. After evaporation of the solvent, the residue was partitioned between EtOAc and water. The organic phase was washed with brine, dried (MgSO₄) and concentrated. Column chromatography (1:1 EtOAc / Hexanes) of the dark brown oil of I-2 as a light brown solid.

$^1$H NMR (CDCl₃) d 6.21 (s, 1H), 4.75 (s, 2H), 2.35 (s, 3H), 1.45 (s, 9H).

HPLC $R_f$=0.71

Scheme 1:
General Synthesis of Bicyclic Pyridone Thrombin Inhibitors

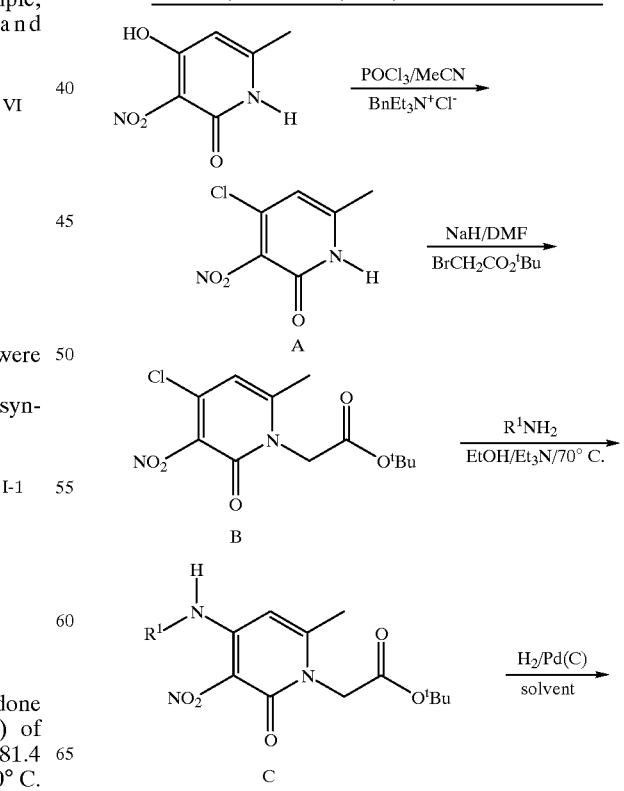

-continued

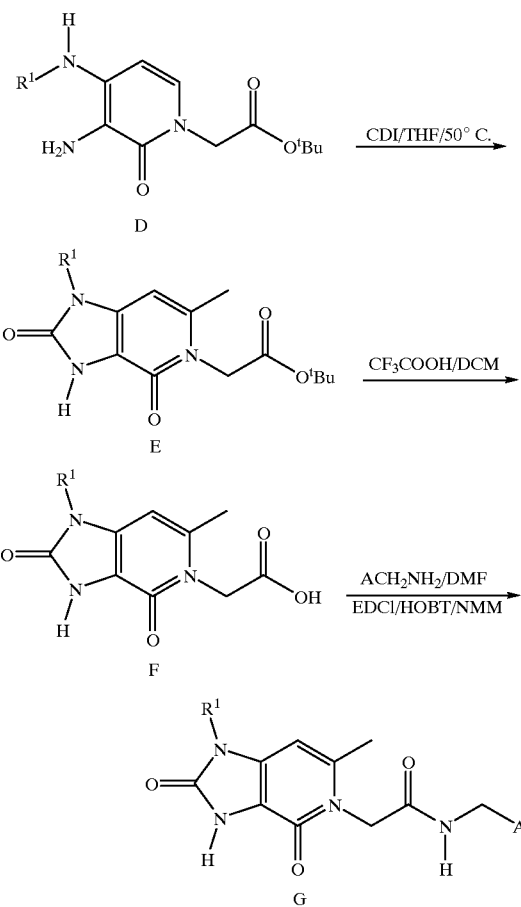

EXAMPLE 1

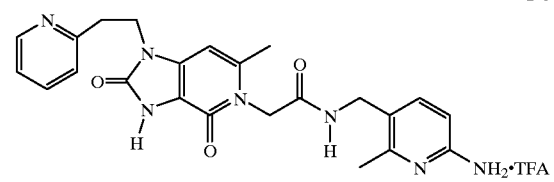

Step A

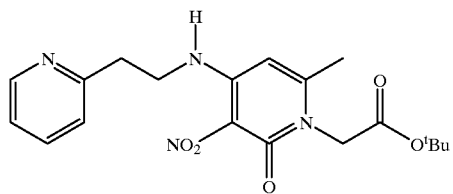

To a solution of pyridone I-2 (740 mg, 2.45 mmol) in 10 mL of EtOH was added 0.35 mL (2.94 mmol) of 2-pyridylethylamine and 0.41 mL (2.94 mmol) of Et$_3$N. The solution was stirred at 70° C. for 1 h, cooled and evaporated to an oil. The residue was partitioned between EtOAc and water and the organic phase was washed with brine, dried (MgSO$_4$) and concentrated to provide the above amine 1-1 as a white solid of sufficient purity for the next step.

$^1$H NMR (CDCl$_3$) d 9.50 (bs, 1H), 8.60 (d, J=2.9 Hz, 1H), 7.64 (t, J=8.2 Hz, 1H), 7.21 (m, 2H), 5.77 (s, 1H), 4.64 (s, 2H), 3.80 (t, J=6.6 Hz, 2H), 3.17 (t, J=6.6 Hz, 2H), 2.25 (s, 3H), 1.47 (s, 9H).

Step B

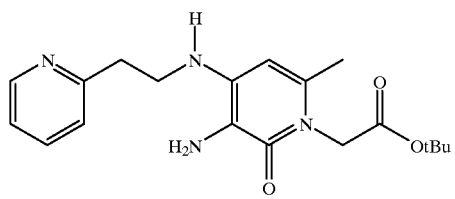

To a solution of the nitro pyridone 1-1 (700 mg, 1.80 mmol) in 40 mL of EtOAc was added 300 mg of 10% Pd(C). The solution was stirred at ambient temperature for 17 h, filtered through Celite and evaporated to an oil. This provided the diamine 1-2 as a white solid which was used directly in the next step without further purification.

$^1$H NMR (CDCl$_3$) d 8.60 (d, J=2.9 Hz, 1H), 7.64 (t, J=8.2 Hz, 1H), 7.17 (m, 2H), 5.80 (s, 1H), 4.75 (s, 2H), 3.60 (t, J=6.6 Hz, 2H), 3.05 (t, J=6.6 Hz, 2H), 2.25 (s, 3H), 1.47 (s,9H).

Step C

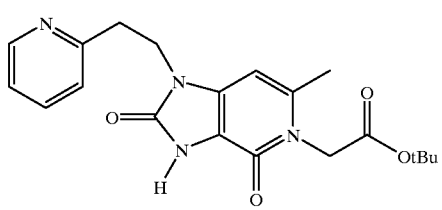

To a solution of amino pyridone 1-2 (500 mg, 1.39 mmol) in 20 mL of THF was added 248 mg (1.53 mmol) of carbonyldiimidazole. The solution was stirred at 50° C. for 16 h, cooled and evaporated to a solid. The residue was partitioned between EtOAc and water and the organic phase was washed with water (3×10 mL), brine (10 mL), dried (MgSO$_4$) and concentrated to provide the above bicycle 1-3 as a white solid.

$^1$H NMR (CDCl$_3$) d 8.60 (d, J=2.9 Hz, 1H), 8.15 (bs, 1H), 7.55 (t, J=8.2 Hz, 1H), 7.10 (m, 2H), 5.90 (s, 1H), 4.75 (s, 2H), 4.15 (t, J=6.6 Hz, 2H), 3.20 (t, J=6.6 Hz, 2H), 2.25 (s, 3H), 1.47 (s, 9H).

Step D

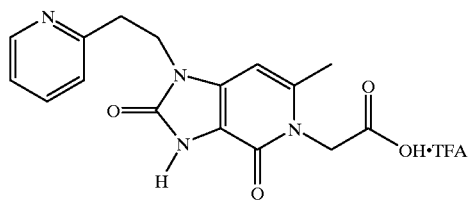

To a solution of the bicyclic pyridone 1-3 (281 mg, 0.73 mmol) in 15 mL of DCM was added 3 mL of trifluoroacetic acid. The solution was stirred at room temperature for 4 h when an additional 6 mL of TFA was added. After stirring for 16 h, the solution was evaporated to an oil which was azeotroped with benzene, EtOAc then ether to provide 1-4 as a white solid.

$^1$H NMR (DMSO-d$_6$) d 8.61 (d, J=2.9 Hz, 1H), 8.05 (bt, 1H), 7.50 (m, 2H), 6.30 (s, 1H), 4.80 (s, 2H), 4.15 (m, 2H), 3.20 (m, 2H), 2.25 (s, 3H), 1.47 (s,9H).

Analysis calculated for C$_{16}$H$_{16}$N$_4$O$_4$.TFA C; 48.87, H; 3.87, N; 12.67 Found: C; 48.69, H; 3.87, N; 12.55

Step E 1-5

To a solution of 1-4 (238 mg, 0.60 mmol) and 170 mg (0.72 mmol) of 5-aminomethyl-2-boc-amino-6-methylpyridine in 2 mL of DMF was added 138 mg (0.72 mmol) of EDCI, 97 mg (0.72 mmol) of HOBT and 0.16 mL (1.44 mmol) of N-methylmorpholine. The reaction mixture was allowed to stir for 16 h before removal of the solvent in vacuo. The mixture was diluted with 2 mL of EtOAc and 2 mL water. The undissolved solid was filtered and air dried to afford the desired product 1-5 as a white solid.

$^1$H NMR (DMSO-d$_6$) d 9.55 (bs, 1H), 8.55 (m, 2H), 7.65 (bt, 1H), 7.20 (m, 2H), 6.25 (s, 1H), 4.70 (s, 2H), 4.20 (s, 2H), 4.15 (m, 2H), 3.10 (m, 2H), 240 (s, 3H), 2.25 (s, 3H), 1.45 (s, 9H).

Analysis calculated for C$_{28}$H$_{33}$N$_7$O$_5$.0.3 H$_2$O C; 60.81, H; 6.12, N; 17.73 Found: C; 60.83, H; 6.28, N; 18.13

Step F 1-6

To a solution of the pyridone 1-5 (274 mg, 0.50 mmol) in 8 mL of DCM was added 4 mL of trifluoroacetic acid. The solution was stirred at room temperature for 4 h and evaporated to a solid. The solid was covered with benzene and azeotroped x2. Ethyl acetate was added and the procedure was repeated. The resulting white solid was stirred in ether and filtered to provide the title compound 1-6 as a white solid.

$^1$H NMR (CD$_3$OD) d 8.70 (bt, 1H), 8.61 (d, J=5.5 Hz, 1H), 8.20 (t, J=7.7 Hz, 1H), 7.85 (d, J=9.1 Hz, 1H), 7.65 (m, 2H), 6.80 (d, J=7.2 Hz, 2H), 6.40 (s, 1H), 4.80 (s, 2H), 4.30 (d, J=4.8 Hz, 2H), 4.20 (t, J=6.6 Hz, 2H), 3.20 (t, J=6.6 Hz, 2H), 2.51 (s, 3H), 2.38 (s, 3H).

Analysis calculated for C$_{23}$H$_{25}$N$_7$O$_3$.2.5 TFA C; 45.90, H; 3.78, N; 13.39 Found: C; 45.71, H; 3.73, N; 13.09

EXAMPLE 2

2-1

2-1 was prepared in an analogous 6-step sequence outlined in Example 1 starting from intermediate I-2 and phenethylamine.

$^1$H NMR (DMSO-d$_6$) d 8.70 (t, J=5.5 Hz, 1H), 7.76 (d, J=9.0 Hz, 1H), 7.71 (bs, 1H), 7.4–7.2 (m, 4H), 6.80 (d, J=9.0 Hz, 1H), 6.33 (s, 1H), 4.69 (s, 2H), 4.15 (d, J=5.5 Hz, 2H), 3.91 (t, J=7.0 Hz, 2H), 3.50 (bs, 2H), 2.89 (t, J=7.0 Hz, 2H), 2.51 (s, 3H), 2.38 (s, 3H).

EXAMPLE 3

3-1

3-1 was prepared in an analogous 6-step sequence outlined in Example 1 starting from intermediate I-2 and aminomethylcyclopropane. The final compound was chromatographed with CHCl$_3$/CH$_3$OH/NH$_4$OH as the eluent to afford the free base 3-1 as a white solid.

$^1$H NMR (DMSO-d$_6$) d 8.40 (bt, 1H), 7.26 (d, J=9.0 Hz, 1H), 6.41 (s, 1H), 6.26 (d, J=9.0 Hz, 1H), 4.65 (s, 2H), 4.15 (d, J=5.5 Hz, 2H), 3.58 (d, J=6.8 Hz, 2H), 2.33 (s, 3H), 2.28 (s, 3H), 1.13 (m, 1H), 0.45 (m, 2H), 0.35 (m, 2H).

EXAMPLE 4

4-1

4-1 was prepared in an analogous 6-step sequence outlined in Example 1 starting from intermediate I-2 and 2-fluorophenethylamine.

$^1$H NMR (CD$_3$OD) d 8.70 (t, J=5.5 Hz, 1H), 7.86 (d, J=9.0 Hz, 1H), 7.25 (m, 2H), 7.05 (m, 2H), 6.80 (d, J=9.0 Hz, 1H), 6.10 (s, 1H), 4.79 (s, 2H), 4.25 (d, J=5.5 Hz, 2H), 4.05 (t, J=7.0 Hz, 2H), 3.05 (t, J=7.0 Hz, 2H), 2.50 (s, 3H), 2.38 (s, 3H).

Analysis calculated for $C_{24}H_{25}N_6O_3F \cdot 2.2$ TFA $\cdot 0.2$ $CH_2Cl_2$ C; 46.99, H; 3.86, N; 11.40 Found: C; 46.99, H; 3.89, N; 11.08

EXAMPLE 5

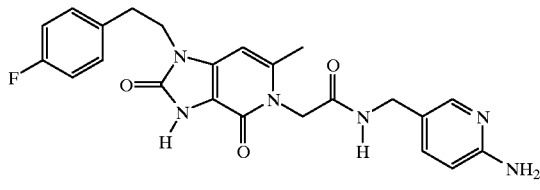

5-1

5-1 was prepared in an analogous 6-step sequence outlined in Example 1 starting from intermediate I-2 and 4-fluorophenethylamine.

$^1$H NMR (CD$_3$OD) d 8.70 (t, J=5.5 Hz, 1H), 7.86 (d, J=9.0 Hz, 1H), 7.25 (m, 2H), 6.95 (m, 2H), 6.80 (d, J=9.0 Hz, 1H), 6.10 (s, 1H), 4.79 (s, 2H), 4.25 (d, J=5.5 Hz, 2H), 4.05 (t, J=7.0 Hz, 2H), 3.05 (t, J=7.0 Hz, 2H), 2.50 (s, 3H), 2.38 (s, 3H).

EXAMPLE 6

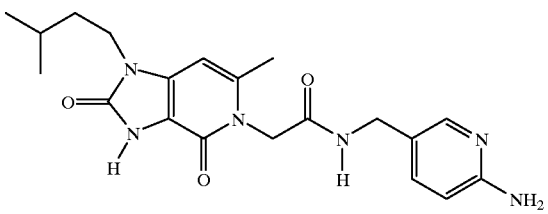

6-1

6-1 was prepared in an analogous 6-step sequence outlined in Example 1 starting from intermediate I-2 and isoamylamine.

$^1$H NMR (CD$_3$OD) d 8.70 (t, J=5.5 Hz, 1H), 7.84 (d, J=9.0 Hz, 1H), 6.80 (d, J=9.0 Hz, 1H), 6.45 (s, 1H), 4.80 (s, 2H), 4.27 (d, J=5.5 Hz, 2H), 3.80 (t, J=7.0 Hz, 2H), 2.51 (s, 3H), 2.38 (s, 3H), 1.80 (m, 1H), 1.60 (t, J=7.0 Hz, 2H), 0.97 (d, J=7.0 Hz, 6H).

Analysis calculated for $C_{21}H_{28}N_6O_3 \cdot 1.4$ TFA C; 49.96, H; 5.18, N; 14.69 Found: C; 49.93, H; 5.44, N; 15.07

EXAMPLE 7

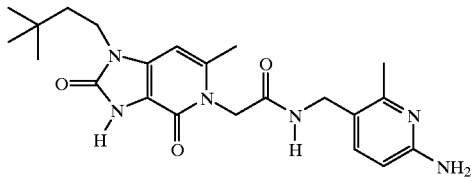

7-1

7-1 was prepared in an analogous 6-step sequence outlined in example 1 starting from intermediate I-2 and 1-amino-3,3-dimethylbutane.

$^1$H NMR (CD$_3$OD) d 8.70 (t, J=5.5 Hz, 1H), 7.84 (d, J=9.0 Hz, 1H), 6.80 (d, J=9.0 Hz, 1H), 6.45 (s, 1H), 4.80 (s, 2H), 4.27 (d, J=5.5 Hz, 2H), 3.80 (t, J=7.0 Hz, 2H), 2.51 (s, 3H), 2.38 (s, 3H), 1.55 (t, J=7.0 Hz, 2H), 0.97 (s, 9H).

Analysis calculated for $C_{22}H_{30}N_6O_3 \cdot 1.5$ TFA C; 47.70, H; 4.93, N; 12.84 Found: C; 47.90, H; 4.53, N; 12.47

EXAMPLE 8

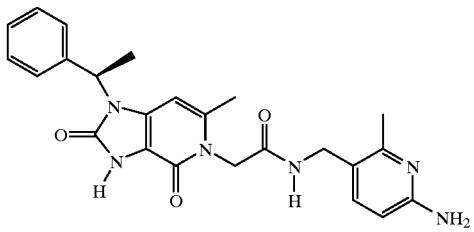

8-1

8-1 was prepared in an analogous 6-step sequence outlined in example 1 starting from intermediate I-2 and (R)-α-methylbenzylamine.

$^1$H NMR (CD$_3$OD) d 8.70 (bs, 1H), 7.82 (d, J=9.0 Hz, 1H), 7.4–7.2 (m, 5H), 6.80 (d, J=9.0 Hz, 1H), 6.13 (s, 1H), 5.72 (m, 1H), 4.80 (s, 2H), 4.35 (s, 2H), 3.50 (bs, 2H), 2.44 (s, 3H), 2.28 (s, 3H), 1.88 (d, J=7.0 Hz, 3H).

Analysis calculated for $C_{24}H_{26}N_6O_3 \cdot 1.5$ TFA C; 49.37, H; 4.13, N; 12.25 Found: C; 49.43, H; 4.44, N; 12.34

EXAMPLE 9

Tablet Preparation

Tablets containing 100.0, 200.0, and 300.0 mg, respectively, of

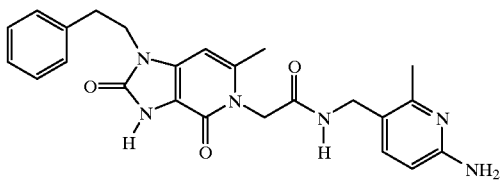

2-1 active compound are prepared as illustrated below:

| Ingredient | Amount-mg | | |
|---|---|---|---|
| Compound 2-1 | 100.0 | 200.0 | 300.0 |
| Microcrystalline cellulose | 160.0 | 150.0 | 200.0 |
| Modified food corn starch | 20.0 | 15.0 | 10.0 |
| Magnesium stearate | 1.5 | 1.0 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 100.0, 200.0, and 300.0 mg, respectively, of active ingredient per tablet.

EXAMPLE 10

Intravenous Solution Preparation

An intravenous dosage form of the above-indicated active compound is prepared as follows:

| | |
|---|---|
| Compound 2-1 | 0.5–10.0 mg |
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

What is claimed is:

1. A compound having the following structure:

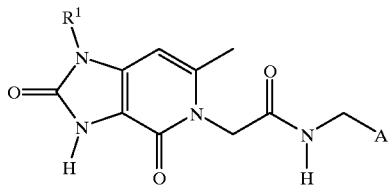

wherein
R$^1$ is selected from the group consisting of
hydrogen,
C$_{1-6}$ alkyl,
C$_{2-6}$ alkenyl,
C$_{2-6}$ alkynyl,
C$_{3-8}$ cycloalkyl,
C$_{3-8}$cycloalkyl C$_{1-6}$alkyl-,
aryl,
aryl C$_{1-6}$ alkyl-,wherein aryl is unsubstituted or substituted with —OH, —NH$_2$, C$_{1-6}$alkyl, C$_{3-8}$cycloalkyl, or halogen, and heteroaryl C$_{1-6}$ alkyl-,wherein heteroaryl is unsubstituted or substituted with —OH, —NH$_2$, C$_{1-6}$alkyl, C$_{3-8}$ cycloalkyl, or halogen;
A is

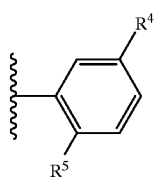

wherein R$^4$ and R$^5$ are independently selected from the group consisting of
hydrogen,
C$_{1-4}$ alkyl,
C$_{2-4}$ alkenyl,
C$_{2-4}$ alkynyl,
C$_{1-4}$ alkoxy,
halogen,
—COOH,
—OH,
—COOR$^7$, where R$^7$ is C$_{1-4}$alkyl,
—CONR$^8$R$^9$, where R$^8$ and R$^9$ are independently hydrogen or C$_{1-4}$alkyl,
—OCH$_2$CO$_2$H,
—OCH$_2$CO$_2$CH$_3$,
—OCH$_2$CO$_2$(CH$_2$)$_{1-3}$CH$_3$,
—O(CH$_2$)$_{1-3}$C(O)NR$^{10}$R$^{11}$, wherein R$^{10}$ and R$^{11}$ are independently hydrogen, C$_{1-4}$alkyl, C$_{3-7}$ cycloalkyl, or —CH$_2$CF$_3$,
—(CH$_2$)$_{1-4}$OH,
—NHC(O)CH$_3$,
—NHC(O)CF$_3$,
—NHSO$_2$CH$_3$,
—SO$_2$NH$_2$;
or A is

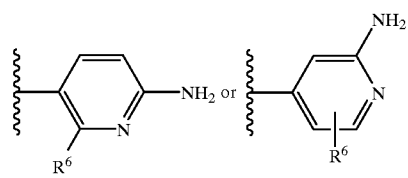

wherein R$^6$ is
hydrogen,
C$_{1-6}$ alkyl,
C$_{2-6}$ alkenyl,
C$_{2-6}$ alkynyl,
C$_{3-8}$ cycloalkyl,
aryl,
aryl C$_{1-6}$alkyl-
wherein aryl is an unsaturated 6-carbon ring, either unsubstituted or substituted with —OH, —NH$_2$, C$_{1-6}$alkyl, C$_{3-8}$ cycloalkyl, or halogen.

and pharmaceutically acceptable salts thereof.

2. The compound of claim 1, and pharmaceutically acceptable salts thereof, wherein A is

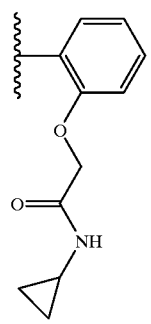 or 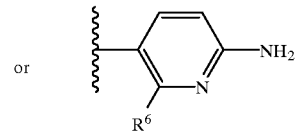

and pharmaceutically acceptable salts thereof.

3. The compound of claim 2, and pharmaceutically acceptable salts, wherein R$^6$ is —CH$_3$.

4. The compound of claim 3, and pharmaceutically acceptable salts, wherein R$^1$ is selected from the group consisting of C$_{1-6}$ alkyl, C$_{3-8}$cycloalkyl C$_{1-6}$alkyl, aryl C$_{1-6}$alkyl and heteroaryl C$_{1-6}$alkyl.

5. The compound of claim 4 selected from the group consisting of:

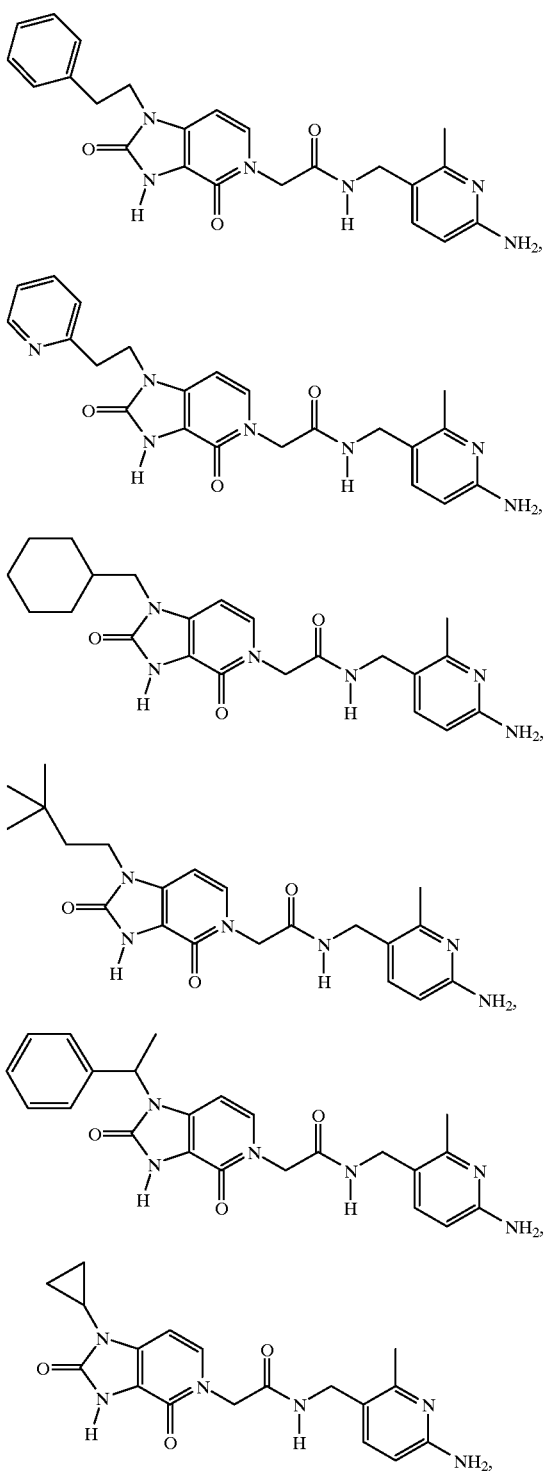

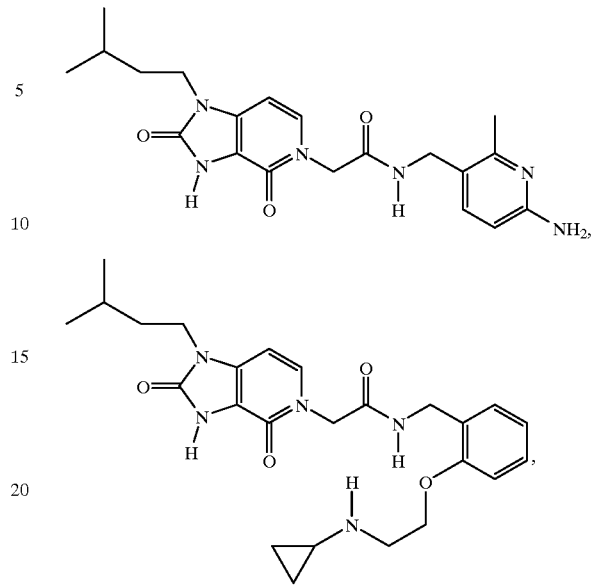

and pharmaceutically acceptable salts thereof.

6. A composition for inhibiting thrombin in blood comprising a compound of claim 1 and a pharmaceutically acceptable carrier.

7. A method for inhibiting thrombin in blood in a mammal comprising administering to the mammal a composition of claim 6.

8. A method for inhibiting formation of blood platelet aggregates in blood in a mammal comprising administering to the mammal a composition of claim 6.

9. A method for inhibiting formation of fibrin in blood in a mammal comprising administering to the mammal a composition of claim 6.

10. A method for inhibiting thrombus formation in blood in a mammal comprising administering to the mammal a composition of claim 6.

11. A method for inhibiting thrombin in stored blood comprising administering to the mammal a composition of claim 6.

12. The use of a compound of claim 1, or a pharmaceutically acceptable salt thereof, in the manufacture of a medicament for inhibiting thrombus formation, preventing thrombus formation, inhibiting thrombin, inhibiting formation of fibrin, and inhibiting formation of blood platelet aggregates, in a mammal.

* * * * *